(12) United States Patent
Raets et al.

(10) Patent No.: US 6,498,250 B2
(45) Date of Patent: Dec. 24, 2002

(54) PROCESS FOR NYLON DEPOLYMERIZATION

(75) Inventors: Leonardus J. G. Raets, Elsloo (NL); Marco J. A. Houben, Sittard (NL); Michel J. G. Huys, Hasselt (BE); Antonius C. Berghmans, Maastricht (NL)

(73) Assignee: DSM N.V., Te Heerlen (NL)

( * ) Notice: Subject to any disclaimer, the term of this patent is extended or adjusted under 35 U.S.C. 154(b) by 0 days.

(21) Appl. No.: 09/983,218

(22) Filed: Oct. 23, 2001

(65) Prior Publication Data

US 2002/0038023 A1 Mar. 28, 2002

Related U.S. Application Data

(63) Continuation of application No. PCT/NL00/00255, filed on Apr. 19, 2000.
(60) Provisional application No. 60/130,639, filed on Apr. 23, 1999.

(30) Foreign Application Priority Data

Apr. 23, 1999 (EP) .............................................. 99201297

(51) Int. Cl.$^7$ .............................................. C07D 201/12
(52) U.S. Cl. ...................................................... 540/540
(58) Field of Search ......................................... 540/540

(56) References Cited

U.S. PATENT DOCUMENTS

| 5,532,487 A | 7/1996 | Brearley et al. | ....... 250/339.12 |
| 5,681,952 A | 10/1997 | Sifniades et al. | ........... 540/540 |

FOREIGN PATENT DOCUMENTS

| WO | 9406763 | 3/1994 |
| WO | 9607092 | 3/1996 |
| WO | 9702481 | 1/1997 |
| WO | 9706137 | 10/1997 |

Primary Examiner—Bruck Kifle

(57) ABSTRACT

The invention relates to a process for nylon depolymerization, in which process a multi-component material, comprising nylon and one or more non-nylon components, is fed to a depolymerization zone in which depolymerization of at least part of said nylon is effected, resulting in a product stream and a residue, said product stream containing monomers of said nylon, said residue containing non-nylon components, wherein the nylon content in the residue is measured and used to control the depolymerization process.

19 Claims, No Drawings

PROCESS FOR NYLON DEPOLYMERIZATION

This is a Continuation of International Application No. PCT/NL00/255 filed Apr. 19, 2000 which designated the U.S. and was published under PCT Article 21(2) in English, and which claims the benefit of U.S. Provisional Application No. 60/130,639, filed Apr. 23, 1999. Both the PCT application and the provisional application are hereby incorporated in their entirety by reference.

BACKGROUND OF THE INVENTION

The invention relates to a process for nylon depolymerization, in which process a multi-component material, comprising nylon and one or more non-nylon components, is fed to a depolymerization zone in which depolymerization of at least part of said nylon is effected, resulting in a product stream and a residue, said product stream containing monomers of said nylon, said residue containing non-nylon components.

Such a process is known from U.S. Pat. No. 5,681,952. In this publication a continuous process is described, where a multi-component, nylon 6 waste material and steam are fed continuously to a reactor. In the reactor depolymerization of nylon 6 takes place, and caprolactam may be recovered overhead, while a nylon 6 depleted bottom stream (residue) may be discharged from the bottoms. Since the composition of the feed material, in particular if the feed material is a multi-component waste material, is usually not constant, it is difficult to control the depolymerization process.

SUMMARY OF THE INVENTION

In view of the above it is an object of the present invention to provide an effective way to control a process for nylon depolymerization, in which process a multi-component material, comprising nylon and one or more non-nylon components, is fed to a depolymerization zone in which depolymerization of at least part of said nylon is effected, resulting in a product stream and a residue, said product stream containing monomers of said nylon, said residue containing non-nylon components.

According to the invention this object is achieved in that the nylon content in the residue is measured and used to control the depolymerization process. We have found that an efficient production of nylon monomers is possible according to the invention since the nylon content of the residue shows considerable variations with relatively small changes in depolymerization process conditions and with relatively small changes in the composition of the multi-component material which is fed to the depolymerization zone.

It is noted that WO-A-9749652 describes a process in which depolymerization of polyamides is effected in the presence of non-polymer contaminants. In the examples a batch process is described in which depolymerization of a glass-filled nylon 6,6, is effected, resulting in a product stream which contains monomers and in a residue, which contains glass fibers. In the examples the extent of the reaction is monitored by analyzing the product stream. The weight of the reactor residue is determined in order to calculate the polymer conversion. The nylon content in the residue is not used to control the depolymerization process.

DETAILED DESCRIPTION

As used herein, "multi-component material" denotes materials or articles that include at least one type of nylon and at least one non-nylon component. By "non-nylon component" is meant any material, excluding nylons, nylon depolymerization products, depolymerization agents, stripping agents, or depolymerization catalysts. By "depolymerizing agent" is meant a solid, liquid or gas that will react with the amide linkage of the nylon to break the linkage, thus lowering the molecular weight of the nylon. Examples of depolymerizing agents are water, steam, alcohols, ammonia, amines. By "stripping agent" is meant a material which is in the gas phase at reaction temperature and which is able to carry away volatile reaction products of the depolymerization, e.g. monomers. The stripping agent may be the depolymerizing agent itself, such as for instance steam, gaseous ammonia or gaseous alcohol, or an inert gas, such as for instance nitrogen. By "depolymerizing catalyst" is meant a solid, liquid or gaseous material which catalyzes the breaking of amide bonds, such as for instance phosphoric acid, boric acid, phosphate salts, alkali metal oxides and alkali metal hydroxides. By "nylon depolymerization products" is meant monomers or oligomers of nylon. The non-nylon components of the "multi-component material" may for instance be non-hydrolyzable polymers, such as for instance polyethylene, polypropylene, polystyrene, and copolymers thereof with butadiene, inorganic or organic materials, such as for instance fillers, pigments, dyes and/or other additives, or other types of materials. The non-nylon components may for instance constitute from about 2 to about 98, preferably from about 5 to about 95, more preferably from about 10 to about 90, and most preferably from about 20 to about 80 weight percent of the multi-component material which is fed to the depolymerization zone. These weight percentages are given with respect to the total weight of the nylon plus the non-nylon components in the multi-component material. The nylon may be any type of nylon, for instance nylon-6, nylon 6,6, nylon 4,6 as well as mixtures thereof. The nylon may for instance constitute from about 2 to about 98, preferably from about 5 to about 95, more preferably from about 10 to about 90, and most preferably from about 20 to about 80 weight percent of the multi-component material which is fed to the depolymerization zone. These weight percentages are given with respect to the total weight of the nylon plus the non-nylon components in the multi-component material. Preferably, at least 40 wt. %, more preferably at least 50 wt. %, in particular at least 75 wt. % and more in particular at least 90 wt. % of the total amount of nylon in the multi-component material is one type of nylon. Preferably, at least 40 wt. %, more preferably at least 50 wt. %, in particular at least 75 wt. % and more in particular at least 90 wt. % of the total amount of nylon in the multi-component material is nylon 6.

The nylon content of the residue may be measured using any technique that allows the determination of the nylon content in the residue. The nylon content in the residue may be expressed by any characteristic from which the amount of nylon in the residue relative to the amount of other components in the residue, preferably relative to the amount of non-nylon components in the residue can be derived. Examples of suitable measurement techniques are high performance liquid chromatography, density measurements, Raman spectroscopy and near infrared spectroscopy. Preferably, measurements techniques are used in which the analysis time is not too long, preferably less than 1 hour. Most preferably, near-infrared spectroscopy is used. Using this technique a quick and acurate measurement of the nylon content is possible.

According to the invention the content of a specific type of nylon in the residue may be determined, for instance the nylon 6 or the nylon 6,6 content. According to the invention it is also possible to measure the total content of all nylons in the residue.

As used herein, "measuring the nylon content of the residue", denotes the determination of the nylon content of the residue during the depolymerization process, either continuously or at intervals. If the nylon content is determined at intervals, it is preferred that frequency of the measurements of the nylon content is sufficiently high that adjustments to the process parameters may be made on time. In order to be able to make adjustments to the process parameters as quickly as possible, it is desired that the time, required for the determination of the nylon content is as short as possible. If the process is very stable, the time interval between two measurements may be longer than if the process is less stable.

The value of the nylon content, e.g. expressed in weight percent nylon, is used to control the depolymerization process. Preferably, the control of the depolymerization process is carried out by comparing the measured nylon content in the residue with a desired value, and adjusting at least one process variable in accordance with the difference between the nylon content in the residue and the desired value. Examples of such process variables are the temperature at which depolymerization is conducted, the rate at which the multi-component material is fed to the depolymerization zone, the feed rate of steam, water alcohol, ammonia and/or amines to the depolymerization zone, the reactor pressure, and/or residence time, but the invention is not limited thereto. The conversion of nylon-6 to caprolactam may for instance be enhanced by increase of steam flow, increase of steam temperature, increase of the temperature at which the depolymerization is conducted, and increase of residence time in the depolymerization zone, which may for instance be achieved by a decrease of the rate at which the multi-component material is fed to the depolymerization zone. If the nylon content in the residue is found to differ too much from the desired value, at least one process variable may be adjusted in such a way that the nylon content in the residue obtains the desired value again. These adjustments may be made manually by an operator, but it is also possible to have the adjustments made in an fully automated way.

The process according to the invention can be carried out batchwise or continuously. The process according to the invention is preferably carried out continuously, since the control of the depolymerization is than particularly effective.

Advantageously, the nylon content in the residue is determined using near infrared spectroscopy. We have found that this technique allows a quick and accurate measurement of the nylon content in the residue, even if the nylon content in the residue is low.

A description of near infrared spectroscopy the application of this technique can for instance be found in manuals of commercial infrared spectrometers. Any type of near infrared spectrometer may be used. A dispersive near infrared spectrometer is preferred.

Typically, a predictive model is created for the value of the nylon content in the residue. Said predictive model gives a correlation between the nylon content of samples of the residue and the near infrared spectra of said samples. In order to create such a predictive model, near infrared spectra of residue samples having various nylon contents may be measured, the nylon contents of said samples having been measured by independent means, for instance by HPLC. Preferably, a spectral pretreatment is applied to the near infrared spectra to obtain, for instance, first or second derivatives of the raw data. However, other spectral pretreatments are also possible. Based on these data, the predictive model may then be calculated using well-known mathematical techniques which, for instance, include Multi-Linear Regression (MLR) and Partial Least Square (PLS) models. However, other mathematical techniques are also possible. For these calculations, commercial software may be used which is often supplied by the supplier of the spectrometer. In order to measure the nylon content of the residue during the process, near infrared spectra of the residue may be obtained. The nylon content of the residue may then be calculated using the predictive model. These calculations are preferably carried out using a computer which is connected to the spectrometer. Preferably, the near infrared spectra of the residue are subjected to a spectral pretreatment to obtain, for instance, first or second derivatives of the raw data.

We have found that the color of the residue may differ for different feed materials. Advantageously, the near infrared spectroscopy is performed using different predictive models for different colors of the residue. In this embodiment different predictive models are created for different colors of the residue. The nylon content of the residue may then be determined by measuring the near infrared spectra, and by calculating the nylon content using a predictive model, said predictive model being selected depending on the color of the residue. Said selection may be done in a fully automated way since the color may usually be derived from the near infrared spectra. The use of different predictive models for different colors of the residue improves the accuracy of the measurements of the nylon content of the residue, if the color of the residue varies. Typical colors of the residue are brown or black, though other colors are possible.

Preferably, near infrared spectra are obtained in the range between 1100–2500 nm. For the determination of the nylon 6 and nylon 6,6 content in the residue, preferably spectral information in the range of 2000 to 2200 nm is used, since in this range the interference with spectra of non-nylon components, such as for instance Styrene-Butadiene Rubber and/or polypropylene is relatively small.

The residue may be available as a continuous molten stream, since the depolymerization is usually conducted at elevated temperatures. The residue may also be available in the solid state. Such a residue may for instance be obtained by cooling and solidifying the molten stream. In a preferred embodiment the near infrared spectroscopy is performed on residue which is molten. This embodiment is in particular advantageous if the measurements of the nylon content in the residue are carried out continuously. In another preferred embodiment the near infrared spectroscopy is performed on residue which is in the solid state, e.g. in flake form. Preferably, the near infrared spectroscopy is performed on residue which is a granulate or powder, the particle diameter preferably being below 1 mm. Such a granulate or powder may for instance be obtained by milling the flakes. This gives a more accurate result, since small inhomogenities are averaged during the milling operation.

Preferably, the nylon content of the multi-component material which is fed to the depolymerization zone is measured, and used to control the depolymerization process. If the data for the nylon content in the multi-component material which is fed to the depolymerization zone and the nylon content in the residue are combined, a very accurate control of the depolymerization is possible, especially when the composition of the feed is not constant. In practice, the nylon content of the feed may vary, if the feed is waste material and if different sources and/or suppliers of the waste material are used. For instance, if the waste material is beneficiated carpet, its nylon content is likely to be dependent on the beneficiation process. The measurement of the nylon content in the multi-component material is not limited to a specific method. Preferably, near infrared spectroscopy is used.

As a result of the depolymerization in the depolymerization zone, a product stream and a residue are obtained.

The product stream contains monomers of the nylon obtained by the depolymerization. Monomers of nylon 6 include $\epsilon$-caprolactam. Monomers of nylon 6,6 include hexamethylenediamine, aminocapronitrile and adiponitrile. Typically, the product stream includes as a major constituent monomers of the nylon. By "major constituent" it is meant that the monomers are the largest constituent of the product stream by weight, excluding depolymerizing agents, stripping agents and depolymerizing catalysts.

The residue contains at least one non-nylon component. By "non-nylon component" is meant any material, excluding nylons, nylon depolymerization products, depolymerization agents, stripping agents, or depolymerization catalysts. Typically, the residue contains residual non-nylon components. By "residual non-nylon components" is meant materials which originate from the non-nylon components in the multi-component material, and which remain after exposure to the conditions at which depolymerization of the nylon is effected. Typically, the residue is depleted of nylon. By "depleted of nylon" is meant that the weight percentage of nylon in the residue is smaller than that in the multi-component material which is fed to the depolymerization zone. Said weight percentages denote the weight percentage of nylon in respect of the total weight of the nylon plus non-nylon components.

In general, it is desirable that the nylon content in the residue is as low as possible, since a lower value of the nylon content in the residue corresponds to a higher conversion of nylon into nylon monomers for a constant flow and contents of the multi-component material. In that case the process parameters may be adjusted, if the nylon content in the residue is found to exceed a certain value. However, it will be clear that it is also possible that the nylon content in the residue is allowed to vary between a certain maximum and minimum value. The desired value of nylon content of the residue will usually be in the range of 0–30 wt. %, preferably from 0.5–20 wt. % and more preferably in the range of 1–10 wt. %. These percentages are given as the weight percentage of the nylon in the residue with respect of the total weight of the nylon plus non-nylon components in the residue.

The depolymerization is not limited to a specific method. Usually, the depolymerization is conducted at a temperature of more than 250° C., preferably more than 280° C., more preferably more than 300° C. Typically, the depolymerizaton is conducted at a temperature of below 400° C., preferably below 350° C., more preferably below 340° C. In a preferred embodiment the depolymerization is carried out in the range of 280–340° C. The depolymerization may be carried out at reduced, atmospheric or increased pressure. Preferably, the depolymerization is carried out in the presence of a depolymerizing agent, such as for instance water, steam, alcohol, ammonia, or amines. Most preferably, the depolymerization is carried out in the presence of water or steam. The depolymerization may be effected in the presence or in the absence of a catalyst. Any type of reactor in which nylon may be depolymerized may be used, such as for instance a continuous stirred tank reactor, a tubular reactor or a series of reactors.

In the depolymerization zone the depolymerization may be effected in many ways. Examples of suitable processes have been described in U.S. Pat. No. 5,681,952, EP-A-737666, WO-A-9749652, WO-A-9618612, WO-A-9406763, WO-A-9706137, WO-A-9618613. In the depolymerization zone, depolymerization may for instance be effected resulting in a vapor stream containing monomers of the nylon and in a residue. The multi-component material may for instance be contacted with a vapor, for instance steam, gaseous ammonia, or gaseous alcohol, resulting in a vapor stream containing monomers of the nylon and in a residue. The nylon content of said residue may then be measured and used to control the depolymerization according to the invention. In another embodiment a mixture comprising water and the multi-component material is subjected to an elevated temperature and pressure to form a liquid aqueous solution which includes monomers of the nylon and a water insoluble portion, and the liquid aqueous solution and the water insoluble portion are separated. Such a process has for instance been described WO-A-9706137, WO-A-9618613. The nylon content of said residue, i.e. the water insoluble portion, may then be measured and used to control the depolymerization according to the invention.

The process according to the invention is in particular suitable if the multi-component material includes nylon 6 and if the depolymerization is conducted in the absence of added catalyst with superheated steam at a temperature of about 250 to 400° C., preferably at a pressure within the range of about 0.1 MPa to about 10 MPa and substantially less than the saturated vapor pressure of water at said temperature. As a result a vapor stream which contains caprolactam is obtained. Said process has been described in detail in U.S. Pat. No. 5,681,952. The nylon content of said residue may then be measured and used to control the depolymerization according to the invention.

Preferably, the multi-component material is nylon-containing waste material or nylon-containing processed waste material, waste material meaning material or articles which has been, is intended to be, or would have been discarded by a consumer, manufacturer, distributor retailer, installer and the like. Preferably, the waste material is waste carpet material, and more preferably waste carpet material that includes nylon 6 face fibre and non-nylon components. Carpets include a face fibre that is adhered to a backing (support) material which may include jute, polypropylene, latex (such as styrene-butadiene rubber (SBR)) and a variety of inorganic materials such as calcium carbonate, clay or hydrated alumina fillers. As used herein, "carpet material" denotes carpet which has not been subjected to any mechanical separation (referred to herein as "whole carpet"), as well as any mixture of carpet components that is a product of separation, mechanical or otherwise, of whole carpet (referred to herein as "beneficiated carpet"). "Waste carpet material" denotes carpet material that has been, is intended to be, or otherwise would have been discarded by a consumer, manufacturer, distributor, retailer, installer and the like.

The following example illustrates a preferred embodiment of the invention.

EXAMPLE

A. Depolymerization Process

Shredded carpet material having nylon 6 face fiber and a backing of polypropylene and calcium-filled Styrene-Butadiene Rubber (SBR) (nylon 6 content of the carpet material about 40 wt. %) was molten at a temperature of 300° C., and continuously fed to a first reactor (flow rate about 65 kg/hour). Superheated steam of 400° C. was continuously blown through the bottom of the reactor, the flow rate of the steam being about 85 kg/hour. The pressure in the first reactor was about 1 MPa. A first caprolactam-containing vapor product stream was recovered from the top of the first reactor. A first molten, nylon-6 depleted residue was continuously withdrawn from the bottom of the first reactor, and fed to a second reactor. Superheated steam of 370° C. was continuously blown through the bottom of the second reactor, the flow rate of the steam being about 60 kg/hour. The pressure in the second reactor was about 1 MPa. A second caprolactam-containing vapor product stream was continuously recovered from the top of the second reactor. A second molten, nylon 6 depleted residue was continuously withdrawn from the bottom of the second reactor (flow rate about 43 kg/hour). Both reactors (Type K-TR160, manufactured by Draiswerke GmbH, Mannheim, Germany) were horizontally positioned, mechanically stirred reactors having a volume of 160 l. During the depolymerization process about 50 vol. % of the reactor volume was filled with molten carpet material. No catalysts were added during the process.

B. Calibration Model

During the start-up of the depolymerization process, the operating conditions were varied to obtain 33 residue samples from the second reactor having various nylon 6 contents (varying between 3 and 27 wt. %). Said residue samples were cooled using a cold surface. The cooled samples were milled to obtain a granulate of which the particles had a diameter of smaller than 1 mm. A fraction of each sample was used for determining the nylon content using High Performace Liquid Chromatography (HPLC). The fraction used for the HPLC measurements was hydrolysed using HCl, and subsequently dissolved in a solvent, after which the HPLC measurements were performed. Another fraction of each sample was used for performing near infrared spectrometry measurements. For this purpose a NIR 6500 spectrometer (Type NIR 6500, manufactured by NIRSystems, Silver Spring Md., USA) with a static sample module was used. Diffuse reflectance spectra were obtained in the range of 1100–2500 nm. In order to create a predictive model giving the correlation between the spectra and the nylon content, the multi-linear regression (MLR) was applied using second derivative spectra at two wavelengths (2048 and 2142 nm) and the nylon contents as determined using the HPLC measurements. Said multi-linear regression was performed using Vision 2.21 Software from NIRSystems (NIRSystems, Silver Spring Md., USA). The standard error for the prediction of the nylon content was less than 1%.

C. Measuring of the Nylon Content and Control of the Depolymerization Process The depolymerization process was carried out under the conditions as described under A, except that the steam temperature which was fed to the second reactor was varied. About every six hours, a sample was taken from the molten residue obtained from the second reactor. Said sample was cooled using a cold surface. The cooled sample was milled to obtain a granulate of which the particles had a diameter of smaller than 1 mm. A diffuse reflectance spectrum was taken from said sample using the NIR 6500 spectrometer, and the nylon content of the sample was calculated using the calibration model as calculated under B.

FIG. 1 shows the nylon content in the residue obtained from the second reactor as a function of time, as measured using near infrared spectroscopy (NIRS), as well as well as the temperature of the steam which is fed to the second reactor. During this experiment the desired range for the nylon content in the residue was between 8 and 10 wt. %. At t=0 h, the nylon content in the residue was within the desired range, and the steam temperature fed to the second reactor was about 375° C. At t=19 h the nylon content in the residue was found to have dropped below 8 wt. %. In order to increase the nylon content in the residue, the steam temperature was lowered to about 350° C. At t=43 h, the nylon content in the residue was found to be within the desired range again. Based on the information of the NIRS measurements the steam temperature was continuously varied in order to keep the nylon content in the residue within the desired range. This example shows that it is possible to measure the nylon content in the residue, to compare the measured value with a desired value, and to adjust process conditions (in this case the temperature of the steam which is fed to the second reactor) accordingly.

What is claimed is:

1. Process for nylon depolymerization, in which process a multi-component material, comprising nylon and one or more non-nylon components, is fed to a depolymerization zone in which depolymerization of at least part of said nylon is effected, resulting in a product stream and a residue, said product stream containing monomers of said nylon, said residue containing non-nylon components, wherein the nylon content in the residue is measured and used to control the depolymerization process.

2. Process according to claim 1, wherein the nylon content in the residue is measured using near infrared spectroscopy.

3. Process according to claim 2, wherein spectral information in the range of 2000 to 2200 nm is used.

4. Process according to claim 2, wherein the near infrared spectroscopy is performed using different predictive models for different colors of the residue.

5. Process according to claim 2, wherein the near infrared spectroscopy is performed on residue which is molten.

6. Process according to claim 2, wherein the infrared spectroscopy is performed on residue which is in the solid state.

7. Process according to claim 6, wherein the near infrared spectroscopy is performed on residue which is a granulate or powder.

8. Process according to claim 1, wherein the nylon content of the multi-component material which is fed to the depolymerization zone is measured, and used to control the depolymerization process.

9. Process according to claim 1, wherein the depolymerization is carried out in the presence of water, steam, an alcohol, ammonia, or an amine.

10. Process according to claim 1, wherein in the depolymerization zone, depolymerization is effected resulting in a vapor stream containing monomers of the nylon and in a residue.

11. Process according to claim 1, wherein in the depolymerization zone the multi-component material is contacted with a vapor.

12. Process according to claim 11, wherein said vapor is steam.

13. Process according to claim 12, wherein the multi-component material includes nylon 6, and that in the depolymerization zone the multi-component material is, in the absence of added catalyst, contacted with superheated steam at a temperature of about 250° C. to about 400° C. and at a pressure within the range of about 0.1 MPa to about 10 MPa and substantially less than the saturated vapor pressure of water at said temperature to obtain a vapor stream which contains caprolactam and a residue.

14. Process according to claim 1, wherein in the depolymerization zone a mixture comprising water and the-multi-component material is subjected to an elevated temperature and an elevated pressure to form a liquid aqueous solution which includes monomers of nylon and a water insoluble portion which includes a mixture of materials other than monomers of nylon and that the liquid aqueous solution and the water insoluble portion are separated, resulting in a product stream and a residue.

15. Process according to claim 1, wherein the multi-component material contains nylon 6, that depolymerization of nylon 6 is effected and that a product stream containing epsilon-caprolactam is obtained.

16. Process according to claim 15, wherein at least 90 wt. % of the nylon in the multi-component material is nylon 6.

17. Process according to claim 1, wherein the multi-component material is multi-component waste material.

18. Process according to claim 17, wherein the multi-component waste material includes waste carpet material.

19. Process according to claim 1, wherein the process is carried out continuously.

* * * * *